United States Patent [19]

Weatherholt

[11] 4,156,145
[45] May 22, 1979

[54] X-RAY SUPPORT

[76] Inventor: Brian R. Weatherholt, P.O. Box 4027, Bay Pines, Fla. 33504

[21] Appl. No.: 797,517

[22] Filed: May 16, 1977

[51] Int. Cl.$^2$ .......................... A61B 6/04; G03B 41/16
[52] U.S. Cl. ...................................... 250/451; 250/456
[58] Field of Search ................................. 250/451, 456

[56] References Cited

U.S. PATENT DOCUMENTS

| | | | |
|---|---|---|---|
| 3,358,141 | 12/1967 | Hoffman et al. | 250/456 |
| 3,971,950 | 7/1976 | Evans et al. | 250/451 |

FOREIGN PATENT DOCUMENTS 2324150  12/1973  Fed. Rep. of Germany ........... 250/456

*Primary Examiner*—Alfred E. Smith
*Assistant Examiner*—T. N. Grigsby
*Attorney, Agent, or Firm*—Stein & Frijouf

[57] ABSTRACT

A patient supporting device is disclosed for positioning a patient relative to a substantially flat surface during x-ray diagnosis or radiation therapy to the patient. The device comprises a support having material properties enabling the propagation of the electromagnetic radiation through the support with only minute attenuation of the electromagnetic radiation. The support has a base surface which is adapted for resting on the flat surface. A support surface on the support is adapted to receive the upper torso of the patient for supporting the patient relative to the flat surface. The invention includes a portion of the support surface being movable to position the patient relative to the flat surface. The device may include an aperture defined in the support between the support surface and base surface for receiving a film sensitive to the electromagnetic radiation. The device is suitable for use as a positioning device for elderly people during an x-ray diagnosis. The movable portion insures the proper positioning of the patient to provide a complete exposure and recording of the patient on the sensitive film. The foregoing abstract is merely a resume of one general application, is not a complete discussion of all principles of operation or applications, and is not to be construed as a limitation on the scope of the claimed subject matter.

10 Claims, 5 Drawing Figures

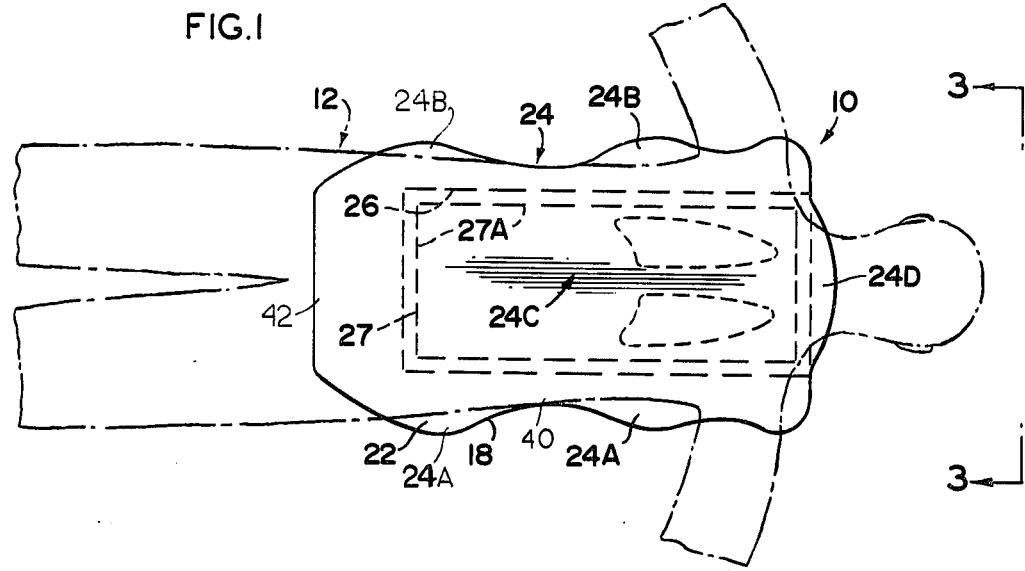
FIG.1
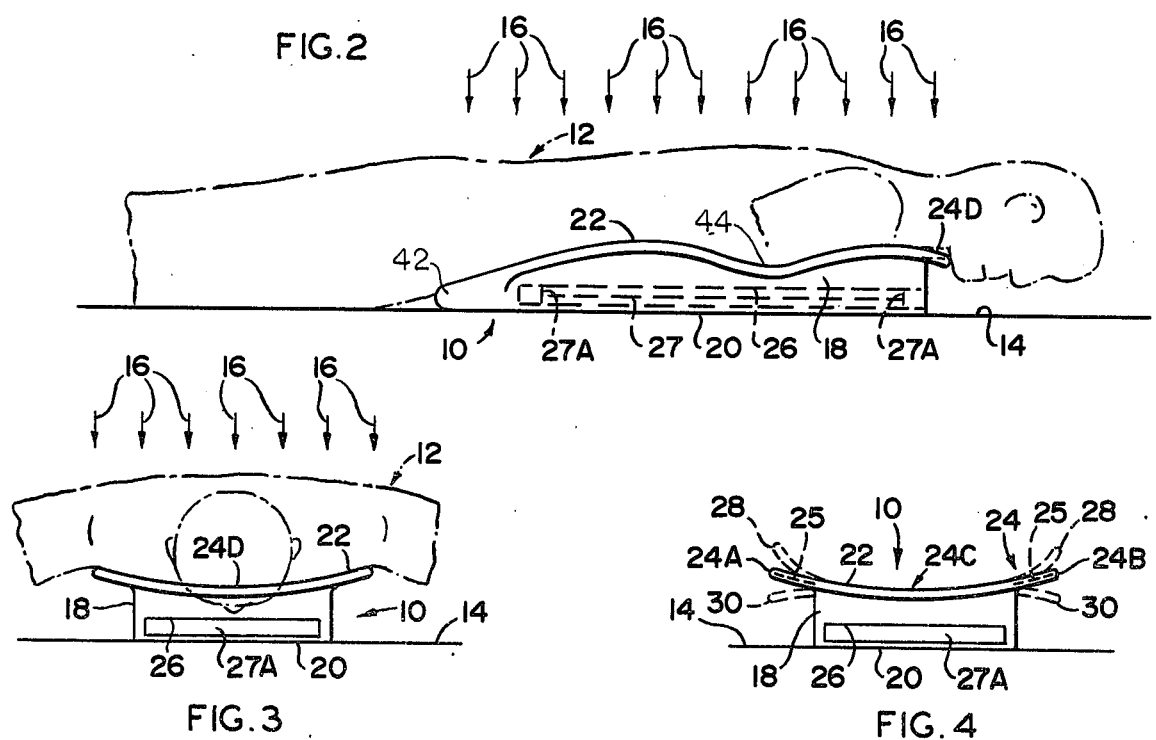
FIG.2
FIG.3
FIG.4
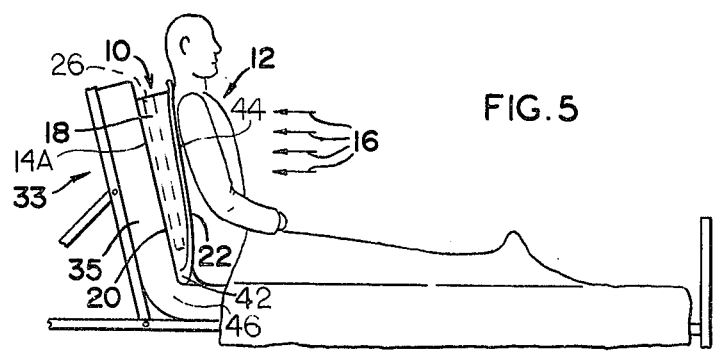
FIG.5

X-RAY SUPPORT

BACKGROUND OF THE INVENTION

1. Field of the Invention

This invention relates to radiant energy and more particularly to means to align or position an object relative to a source of radiant energy.

2. Description of the Prior Art

Various supporting devices have been developed over the years for the medical industry. In many situations, a patient must be immobilized in order to perform a surgical treatment while the patient is subjected to only a partial or a local anesthetic. Other supporting devices have been devised for the medical industry for positioning a patient in an unconventional position in order to administer surgical treatments or therapy to the patient. Most of these supporting devices have been specifically designed to aid the administration of a particular type of treatment to the patient. Accordingly, various types of medical supporting devices are available, each of which is unique to a particular problem of the medical profession.

An important field of the medical profession for both diagnosis and therapy is the field of radiation. In general, medical radiology is primarily concerned with x-ray and Gamma-Ray radiation for both the diagnosis and the treatment of disease. X-rays have long been used for detecting fractures of bones as well as tumors and other foreign materials within the human body. Gamma-Ray treatment has been used in recent years for the selective destruction of undesirable tissues within the human body.

In both the x-ray and Gamma-Ray treatment, it is imperative that the electromagnetic radiation be carefully directed to the area of concern within the patient. Accordingly, the patient must be properly positioned and immobilized during the radiation treatment in order to insure that the radiation propagates through the selected part of the patient. For example, during the exposure of an x-ray sensitive film of the chest of a person, the technician must properly position the x-ray film relative to the patient so that the x-ray radiation will propagate through the chest cavity of the patient and impinge upon the x-ray sensitive film. In many cases, the patient's body must be established in an arched manner in order to produce an image on the x-ray film which properly depicts the area of interest of the chest cavity.

It is difficult for an elderly person to maintain an arched position for the time required for the technician to retire to a radiation safe position and energize the x-ray tube. Unfortunately, the technician does not know until after the film is developed if the patient has moved and the x-ray image is incomplete. By this time, the patient may have been returned to another area of the medical center and must be brought back to the x-ray room for a second x-ray diagnosis. The second x-ray treatment adds to the burden of medical centers which are already plagued with increased costs for medical treatment.

In many cases a patient may be so weak that the x-ray treatment must be administered while the patient is in bed. The prior art has failed to develop a portable x-ray support for use both on a conventional x-ray table and on a bed.

Therefore it is an object of this invention to provide an apparatus which overcomes the aforementioned inadequacies of the prior art devices and provides an improvement which is a significant contribution to the advancement of the radiant energy art.

Another object of this invention is to provide a device for positioning a patient relative to a substantially flat surface during the administration of electromagnetic radiation comprising a support having material properties enabling the propagation of electromagnetic radiation through the support with only minute attenuation of the electromagnetic radiation.

Another object of this invention is to provide a device for positioning a patient relative to a substantially flat surface during the administration of electromagnetic radiation comprising a support having a base surface adapted for resting on the substantially flat surface and a support surface on the support adapted to receive the upper torso of a patient for supporting the patient relative to the flat surface.

Another object of this invention is to provide a device for positioning a patient relative to a substantially flat surface during the administration of electromagnetic radiation comprising a support with movement means establishing a movable portion of a support surface relative to the remainder of the support surface to position the patient relative to the flat surface.

Another object of this invention is to provide a device for positioning a patient relative to a substantially flat surface during the administration of electromagnetic radiation comprising a support with a base surface adapted for resting on the substantially flat surface and a support surface for supporting the patient relative to the flat surface with an aperture defined in the support for receiving a film sensitive to the electromagnetic radiation.

Another object of this invention is to provide a device for positioning a patient relative to a substantially flat surface during the administration of electromagnetic radiation to the patient wherein the movable portion of support surface includes a first and a second movable portion established on opposite lateral edges of the support means.

Another object of this invention is to provide a device for positioning a patient relative to a substantially flat surface during the administration of electromagnetic radiation to the patient including movable portions being established of a flexible material.

Another object of this invention is to provide a device for positioning a patient relative to a surface during the administration of electromagnetic radiation to the patient which is adaptable for use both on any conventional x-ray table in addition to being operable on a conventional hospital bed.

Another object of this invention is to provide a device for positioning a patient relative to a surface during the administration of electromagnetic radiation to the patient which is portable and permits anterior-posterior and posterior-anterior x-rays on a hospital bed.

Other objects and a fuller understanding of this invention may be had by referring to the summary of the invention, the description and the claims, taken in conjunction with the accompanying drawings.

SUMMARY OF THE INVENTION

The invention may be incorporated into a device for positioning a patient relative to a flat surface during the administration of electromagnetic radiation to the patient. The invention includes support means having material properties enabling propagation of electromagnetic radiation through the support means with only minute attenuation of the electromagnetic radiation. The support means has a base surface adapted for resting on the flat surface. A support surface on the support means is adapted to receive the upper torso of the patient for supporting the patient relative to the flat surface. A movable portion means is established on the support surface to be movable relative to the remainder of the support surface to position the patient relative to the flat surface.

In a specific example of the instant invention, the movable portion means of the support surface may include a first and a second movable portion established on opposite lateral edges of the support means. The movable portion means may include the support surface being flexible for enabling movement of the movable portion means relative to the support means.

The invention may include aperture means defined in the support means for receiving a film sensitive to the electromagnetic radiation. The aperture means may be defined in one end of the support means with a tapered edge located at the other end of the support means for gradually displacing the patient relative to the substantially flat surface. The support surface may include a depressed region for receiving the chest of the patient when the patient is leaning on the support. The depressed region is adapted for providing proper support to the back region of the patient. The support surface is generally dish-shaped for maintaining the patient relative to the device. Optional reinforcement means may be established between the movable portion and the support means for supporting the movable portions.

This invention accordingly comprises an apparatus possessing the features, properties and the relation of elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which:

FIG. 1 is a top elevational view showing a medical supporting device supporting a patient on a substantially horizontal flat surface;

FIG. 2 is a side elevational view of the invention shown in FIG. 1;

FIG. 3 is an end view along line 3—3 of the invention shown in FIGS. 1 and 2;

FIG. 4 is an end elevational view of the invention shown in FIG. 1-3 illustrating movement of movable portions of the support means; and FIG. 5 is a side elevational view of the medical support illustrated in FIGS. 1-4 showing a patient being supported relative to a substantially vertical surface.

Similar reference characters refer to similar parts throughout the several view o the drawings.

DETAILED DESCRIPTION

FIGS. 1-3 illustrate top, side and end elevational views of the instant invention showing a device 10 for positioning a patient 12 relative to a substantially horizontal surface 14. The device 10 supports the patient 12 during the administration of electromagnetic radiation represented by arrows 16 to the patient 12. The substantially horizontal surface 14 may be a conventional x-ray table or x-ray bed but it should be understood that any substantially flat surface may receive the device 10 as illustrated by the substantially vertical surface 14A in FIG. 5.

The device 10 includes support means 18 having material properties enabling the propagation of the electromagnetic radiation through the support means 18 with only minute attenuation of the electromagnetic radiation. The support means 18 is preferably made of a plastic material which is strong enough to support a patient while being simultaneously lightweight and optically transparent to the electromagnetic radiation. It should also be realized that a rubber type material may also be suitable for construction of the support means 18.

The support means 18 includes a base surface 20 shown as a substantially flat surface for resting on the horizontal surface 14. The support means 18 also includes a support surface 22 adapted to receive the upper torso of the patient 12 for supporting the patient 12 relative to the horizontal surface 14. The patient in FIGS. 1-3 is shown lying in a face down position (posterior-anterior) but it is equally understood that the support 22 may receive the back region of the patient 12.

The support means 18 includes aperture means 26 for receiving a film 27 sensitive to the electromagnic radiation. In this embodiment, the film 27 is shown established in a film frame 27A which is insertable within the aperture 26. The electromagnetic rays shown by the arrows 16 pass through the patient 12 to expose the x-ray sensitive film 27 thereby imagining the x-ray film with the internal structure of the patient 12. The device 10 secures the patient 12 relative to the x-ray film 27 to substantially reduce the number of incomplete x-rays taken, especially of elderly people.

A significant aspect of the invention resides in movement means 24 shown as movable portion means 24A and 24B in FIG. 1 which are movable relative to the remainder 24C of the support surface 22 for positioning the patient 12 relative to the horizontal surface 14. The movable portions 24A and 24B are established on opposed lateral edges of the support means 18 and include the support surface 22 being flexible for enabling movement of the movable portions 24A and 24B relative to the remainder of the support means 18. FIG. 4 more accurately illustrates the movement of movable portions 24A and 24B between an upper position 28 and a lower position 30 both shown in phantom. The invention shown in FIG. 4, includes the movable portions 24A and 24B being movable yet partially rigid to retain the position set by the x-ray technician. For example, if an x-ray technician adjusts either or both of the movable portions 24A and 24B into the upper position 28, then the movable portions 24A and 24B will remain in that position and support the patient 12. An optional reinforcement means shown as a flexible metallic material shown in phantom as 25 may be insertable within the support surface 22 to further add mechanical strength and rigidity to the movable portions 24A and 24B. However, it is understood that the metallic material 25 should be located outside of the area of interest of the diagnosis or the treatment by the electromagnetic radiation. An optional movable portion 24D may be incorporated into the device 10 to aid positioning the patient 12 in either the face down or the face-up position. Movable portion 24D is adjustable between the phantom positions shown in FIG. 2.

The device 10 includes a narrowed region 40 interposed between movable portions 24A and 24B. Each of the five movable portions 24A, 24B and 24D may be independently adjusted to properly position the patient 12. A tapered end 42 gradually displaces the patient 12 from the flat surface 14 to comfortably rest the patient. The support surface 22 includes a depressed region 44 adapted for receiving the chest of the patient when the patient is in the face down position as shown in FIG. 1-3. The depressed region 44 simultaneously provides proper support to a patient in the face up position (not shown) or in the generally vertical position shown in FIG. 5. FIGS. 3 and 4 illustrate the generally dish shape of the support surface 22 which maintains the patient in the proper position relative to the device 10.

FIG. 5 is an elevational view of the device 10 supporting the patient in a generally vertical position on a conventional bed 33. The bed 33 is shown with the upper region 35 adjusted to an upright position as is well known in the art. The base surface 20 of the support means 18 is established adjacent the upper region 35 of the bed 33. The tapered end cooperates with the fold 46 in the bed mattress to comfortably support the patient 12. The depressed region 44 although capable of receiving the chest of the patient, still provides proper support to the upright patient. The movable portions 24A and 24B maintain the patient in the upright position and eliminate the lateral movement of the patient during the x-ray process. The aperture means 26 is conveniently located behind the patient enabling the technician to image multiple x-ray films without moving the patient. Multiple x-ray films may also be taken without moving the patient when used in the face up or face down horizontal position as can be seen in FIGS. 1-4.

It should be appreciated that the device 10 is a lightweight portable support which may be used in a fully equiped x-ray center as well as being used on a conventional bed or other flat surface. The device 10 is capable of supporting both the chest or the back of a patient in either a vertical or a horizontal position. Obviously, the device is equally adapted for supporting the patient at angles between a horizontal and a vertical position.

The invention finds a substantial application in the area of x-ray diagnosis. Device 10 may be established on an x-ray table or a conventional bed to position the patient relative to the x-ray tube. Accordingly, the technician need only position the patient 12 on the support device 10 and adjust the x-ray tube to properly image the patient on the film 27. The movable portions 24A and 24B insure that the patient 12 remains in the proper position on the device 10 while the technician retires to energize the x-ray tube. If an elderly patient is placed on a x-ray table or a bed, the patient may move during the time the technician is retiring to energize the x-ray tube. The instant invention eliminates this possibility by keeping the patient 12 in the proper position. It also should be noted that the support is properly contoured to make the patient comfortable during the x-ray process. The use of the invention substantially reduces the possibility of movement by the patient and accordingly substantially reduces the number of incomplete images on the x-ray film 27.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention.

Now that the invention has been described, What is claimed is:

1. A device for positioning a patient relative to a substantially flat surface during the administration of electromagnetic radiation to the patient, comprising in combination:

support means having material properties enabling propagation of the electromagnetic radiation through said support means with only minute attenuation of the electromagnetic radiation;

said support means having a base surface adapted for resting on the substantially flat surface;

a support surface on said support means adapted to receive the upper torso of the patient for supporting the patient relative to the flat surface; and movement means establishing movable portion means of said support surface relative to the remainder of said support surface to position the patient relative to the horizontal surface wherein said movement means is movable yet partially rigid to retain the position set by a technician.

2. A device as set forth in claim 1, including aperture means defined in said support means for receiving a film sensitive to the electromagnetic radiation.

3. A device as set forth in claim 1, wherein the electromagnetic radiation is x-ray radiation; and aperture means defined in said support member for receiving an x-ray sensitive film.

4. A device as set forth in claim 1, wherein said movable portion means of said support surface includes a first and a second movable portion established at opposed lateral edges of said support means.

5. A device as set forth in claim 1, wherein said movable portion means includes said support surface being flexible for enabling movement of said movable portion relative to said support means.

6. A device as set forth in claim 1, wherein said movement means includes said movable portion being a flexible material; and reinforcement means established between said movable portion and said support means for supporting said movable portion.

7. A device as set forth in claim 1, wherein said support surface is generally dish shaped for maintaining the patient relative to the device.

8. A device as set forth in claim 1, wherein said support means includes a tapered edge for gradually displacing the patient relative to the substantially flat surface.

9. A device as set forth in claim 1, wherein said support surface includes a depressed region for receiving the chest of the patient.

10. A device as set forth in claim 1, including aperture means defined in one end of said support means for receiving a film sensitive to the electromagnetic radiation; and said support means including a tapered edge at the other end of said support means for gradually displacing the patient relative to the substantially flat surface.

* * * * *